US009163036B2

(12) United States Patent
Savonnet et al.

(10) Patent No.: US 9,163,036 B2
(45) Date of Patent: Oct. 20, 2015

(54) MIL-53-AL-N₃ ORGANIC/INORGANIC HYBRID SOLID PROVIDED WITH AN AZIDE FUNCTION AND METHOD FOR MANUFACTURING SAME

(75) Inventors: Marie Savonnet, Lyons (FR); David Farrusseng, Belmont D'azegues (FR); Catherine Pinel, Lyons (FR); Delphine Bazer-Bachi, Irigny (FR); Nicolas Bats, Saint Symphorien D'ozon (FR); Vincent Lecocq, Orlienas (FR)

(73) Assignees: CNRS, Paris Cedex (FR); IFP ENERGIES NOUVELLES, Rueil-Malmaison Cedex (FR)

( * ) Notice: Subject to any disclaimer, the term of this patent is extended or adjusted under 35 U.S.C. 154(b) by 174 days.

(21) Appl. No.: 13/503,286

(22) PCT Filed: Oct. 6, 2010

(86) PCT No.: PCT/FR2010/000667
§ 371 (c)(1),
(2), (4) Date: Aug. 9, 2012

(87) PCT Pub. No.: WO2011/048280
PCT Pub. Date: Apr. 28, 2011

(65) Prior Publication Data
US 2012/0296103 A1    Nov. 22, 2012

(30) Foreign Application Priority Data
Oct. 23, 2009  (FR) .................................... 09 05105

(51) Int. Cl.
*C07F 5/06*    (2006.01)
(52) U.S. Cl.
CPC ...................... *C07F 5/069* (2013.01)
(58) Field of Classification Search
USPC .................................. 556/1; 552/4
See application file for complete search history.

(56) References Cited

U.S. PATENT DOCUMENTS

| 7,893,002 | B2 * | 2/2011 | Farrusseng et al. | 502/4 |
| 8,586,774 | B2 * | 11/2013 | Savonnet et al. | 556/1 |
| 8,940,905 | B2 * | 1/2015 | Savonnet et al. | 548/104 |
| 2006/0287190 | A1 * | 12/2006 | Eddaoudi et al. | 502/60 |
| 2010/0293843 | A1 * | 11/2010 | Bazer-Bachi et al. | 44/398 |

OTHER PUBLICATIONS

Marie Vougo-Zanda et al. (Inorganic Chemistry, vol. 47, No. 24, 2008,11535-42).*
Brunel, Daniel. (Microporous and Mesoporous Materials 27 (1999) 329-344).*
Savonnet, M. et al., "Generic Postfunctionalization Route from Amino-Derived Metal-Organic Frameworks," Journal of the American Chemical Society, Apr. 7, 2010, vol. 132, No. 13, pp. 4518-4519; International Search Report issued in corresponding PCT/FR2010/000667 on Jan. 21, 2011.
Wang, Z. et al., "Accessing Postsynthetic Modification in a Series of Metal-Organic Frameworks and the Influence of Framework Topology on Reactivity," Inorganic Chemistry, 2009, vol. 48, No. 1, pp. 296-306; International Search Report issued in corresponding PCT/FR2010/000667 on Jan. 21, 2011.
Ahnfeldt, T. et al., "Synthesis and Modification of a Functionalized 3D Open-Framework Structure with MIL-53 Topology," Inorganic Chemistry, Apr. 6, 2009, vol. 48, No. 7, pp. 3057-3064; International Search Report issued in corresponding PCT/FR2010/000667 on Jan. 21, 2011.
International Search Report issued in corresponding PCT/FR2010/000667 on Jan. 21, 2011.

* cited by examiner

*Primary Examiner* — Sabiha N Qazi
(74) *Attorney, Agent, or Firm* — Millen, White, Zelano & Branigan, P.C.

(57) ABSTRACT

The invention describes a crystallized hybrid solid with an organic-inorganic matrix, of a three-dimensional structure, containing an inorganic network of aluminum-based metal centers that are connected to one another by organic ligands that consist of the entity —$O_2C$—$C_6H_3$—$N_3$—$CO_2$—. Said solid is called MIL-53-Al—$N_3$ and has an X-ray diffraction diagram as given below.

13 Claims, 1 Drawing Sheet

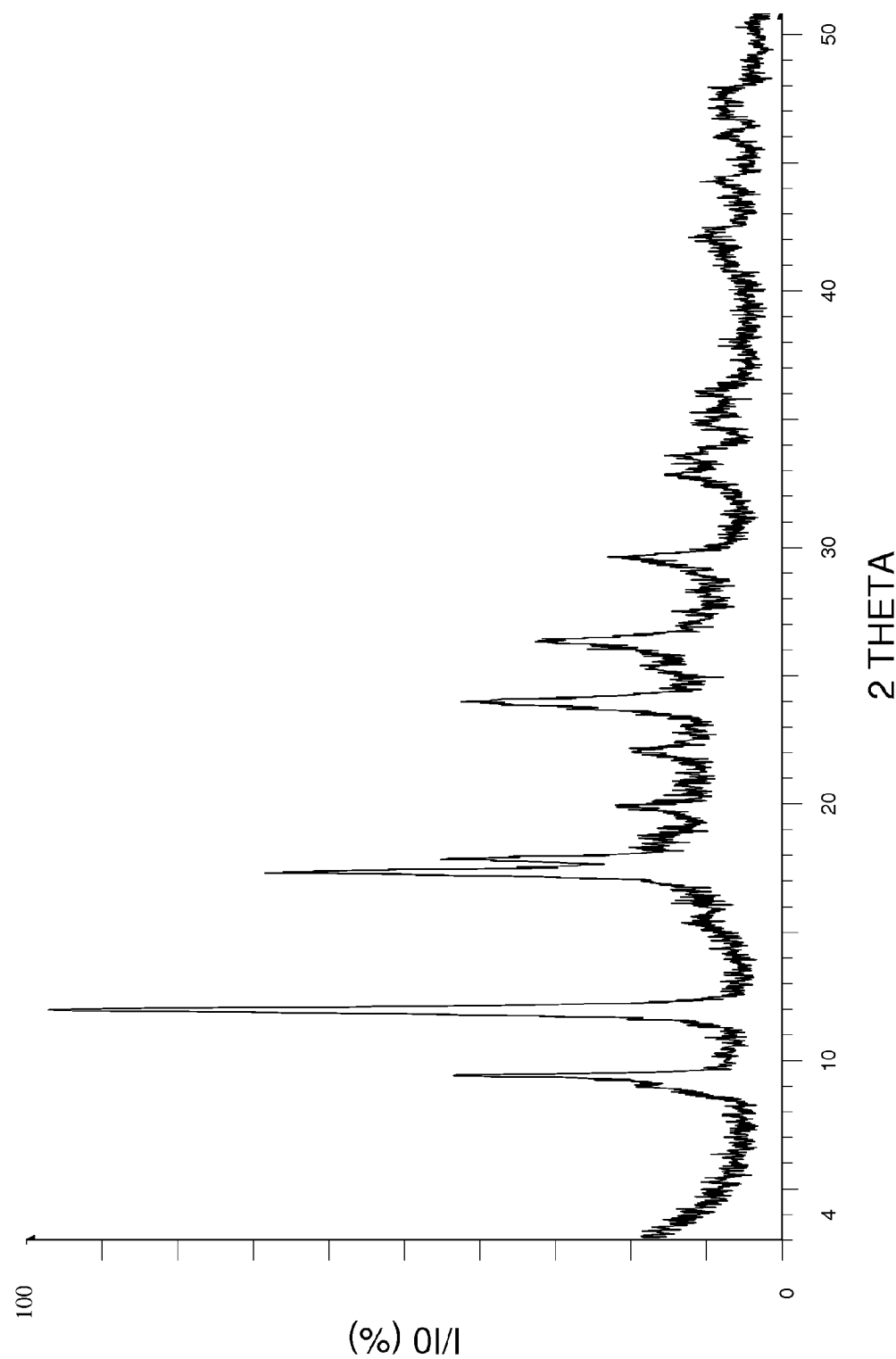

MIL-53-AL-N₃ ORGANIC/INORGANIC HYBRID SOLID PROVIDED WITH AN AZIDE FUNCTION AND METHOD FOR MANUFACTURING SAME

TECHNICAL FIELD OF THE INVENTION

This invention relates to a new crystallized hybrid solid with an organic-inorganic matrix, of a three-dimensional structure, and to the process for its preparation starting from the MIL-53-Al—$NH_2$ crystallized hybrid solid with an organic-inorganic matrix that is already described in the literature. Said new solid, object of this invention, carries an azide group and is called MIL-53-Al—$N_3$ in the description below. Said MIL-53-Al—$N_3$ solid has a crystalline structure that is identical to the one of the MIL-53-Al—$NH_2$ solid from which it is obtained by a post-synthesis functionalization method. Said MIL-53-Al—$N_3$ solid is advantageously used in applications as a catalyst or adsorbent or else as an intermediate compound for obtaining functionalized crystallized hybrid solids with an organic-inorganic matrix.

STATE OF THE ART

The modification of materials by functionalization is a stage that is often necessary for the development of solids that have suitable properties for a given application. Actually, it may be desirable to improve the physico-chemical properties of a material, by modifying its surface, for example, so that the new properties that are obtained after modifications are more suitable for separation or catalysis applications.

One of the means that is commonly used to modify the surface of a material consists in reacting the functional groups that are initially present on its surface by entities that have the desired groups for the application being considered. The groups that are present on the surface of a material can be hydroxyl groups (—OH) or any other group (amino —$NH_2$ or —NH—, for example) that it is desired to modify so as to orient the chemical reactivity of the surface of the material. The reagents that are used will have the necessary functionalities for reacting with the groups that are initially present on the surface of the material, and the result of the reaction will be a new chemical group that has the desired reactivity. One example of such a transformation consists in reacting the hydroxyl groups of the surface of a silica by a silane that carries an amine group (D. Brunel, *Microporous and Mesoporous Materials*, 1999, 27, 329-344). Thus, the hydroxyl group is transformed into an amine group that is better able to catalyze basic reactions or to collect $CO_2$, for example. This methodology can be applied to any material that initially has reactive groups. These materials can be oxides, zeolites, or else organic/inorganic hybrid materials, also called coordination polymers.

These coordination polymers, of which the first were described in the 1960's, are the object of a growing number of publications. Actually, the effervescence around these materials made it possible to attain an advanced structural diversity in little time (Férey, G., l'actualité chimique [Chemical Issues], January 2007, No. 304). Conceptually, the porous hybrid solids with an organic-inorganic mixed matrix are quite similar to porous solids with an inorganic skeleton. Like the latter, they combine chemical entities by giving rise to a porosity. The primary difference resides in the nature of these entities. This difference is particularly advantageous and is at the origin of the entire versatility of this category of hybrid solids. Actually, the size of the pores becomes, by using organic ligands, adjustable by means of the length of the carbon-containing chain of said organic ligands. The framework, which in the case of inorganic porous materials can accept only some elements (Si, Al, Ge, Ga, and optionally Zn), can, in this case, collect all of the cations except for the alkalines. For the preparation of these hybrid materials, no specific structuring agent is required; the solvent provides this effect by itself.

It therefore clearly appears that this family of hybrid materials makes possible a multiplicity of structures and consequently comprises solids that are finely adapted to the applications for which they are designed.

The coordination polymers comprise at least two elements that are called connectors and ligands whose orientation and number of connecting sites are decisive in the structure of the hybrid material. From the diversity of these ligands and connectors, an immense variety of hybrid materials is born, as has already been specified.

Ligand is defined as the organic part of the hybrid material. These ligands are most often di- or tricarboxylates or derivatives of pyridine. Some commonly encountered organic ligands are shown below: bdc=benzene-1,4-dicarboxylate, btc=benzene-1,3,5-tricarboxylate, ndc=naphthalene-2,6-dicarboxylate, bpy=4,4'-bipyridine, hfipbb=4,4'-(hexafluoroisopropylidene)-bisbenzoate, cyclam=1,4,8,11-tetraazacyclotetradecane.

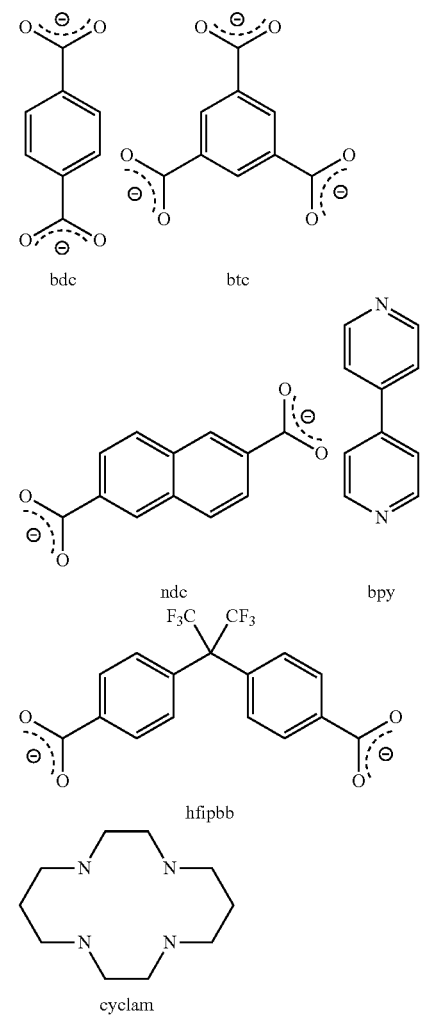

Connector is defined as the inorganic entity of the hybrid material. It may be a cation by itself, a dimer, trimer, or tetramer, or else a chain or a plane.

Within the framework of this invention, the ligand that is used is 2-amino-terephthalic acid ($NH_2$—$H_2$-bdc). For its part, the inorganic entity that plays the role of connector is aluminum.

The teams of Yaghi and Férey have thus described a large number of new hybrid materials (series of MOF—"Metal Organic Framework"—and series of MIL—"Materiaux de l'Institut Lavoisier [Lavoisier Institute Materials]"—respectively). Numerous other teams have followed this path, and today, the number of new hybrid materials described is expanding rapidly. Most often, the purpose of the studies is to develop ordered structures, having extremely large pore volumes, good thermal stability, and adjustable chemical functionalities.

For example, Yaghi et al. describe a series of boron-based structures in the patent application US 2006/0154807 and indicate their advantage in the field of gas storage. The U.S. Pat. No. 7,202,385 discloses a particularly complete summary of the structures that are described in the literature and perfectly illustrates the multitude of materials already existing today.

The preparation of organic-inorganic hybrid materials that exhibit a reactive organic group (grafted MOF) can be implemented by two primary paths: functionalization by self-assembly and functionalization by post-modification. The functionalization by self-assembly is implemented by bringing an organic ligand that has the desired reactive group (graft) into the presence of an inorganic compound that has the role of connector. This functionalization method is often difficult to implement because of problems linked to the solubilization and the reactivity of the functionalized ligands. In particular, the ligands that carry an —OH, —COOH or —$NH_2$ group run the risk of interacting with the inorganic compound (connector) that then leads to non-isostructural solids with non-grafted reference MOF. The functionalization by post-modification is an advantageous alternative method that does not exhibit functionalization limits by self-assembly. The functionalization by post-modification consists in directly modifying the organic group of at least one type of ligand that is present in the MOF by a chemical reaction (grafting), more specifically in replacing the initial organic group by an organic group whose reactivity is preferred for a subsequent application. This method suggests the presence on the initial MOF of an organic group that is accessible and reactive for grafting. In the literature, the organic-inorganic hybrid materials that carry a ligand with an —$NH_2$ amino group such as DMOF-1-$NH_2$ (Z. Q. Wang; K. K. Tanabe; S. M. Cohen, *Inorganic Chemistry*, 2009, 48, 296-306) are described as good substrates for the grafting of numerous groups, in particular aldehydes, isocyanates, and acid anhydrides.

DESCRIPTION OF THE INVENTION

This invention has as its object a new crystallized hybrid solid with an organic-inorganic matrix that has a three-dimensional structure. This new solid is called MIL-53-Al—$N_3$. It contains an inorganic network of aluminum-based metal centers that are connected to one another by organic ligands that consist of the entity —$O_2C$—$C_6H_3$—$N_3$—$CO_2$—.

The MIL-53-Al—$N_3$ crystallized hybrid solid according to the invention has an X-ray diffraction diagram that includes at least the lines that are recorded in Table 1. This diffraction diagram is obtained by radiocrystallographic analysis by means of a diffractometer by using the conventional method of powders with the K$\alpha$1 radiation of copper ($\lambda$=1.5406 Å). Starting from the position of diffraction peaks shown by the angle 2$\theta$, the reticular equidistances $d_{hkl}$ that are characteristic of the sample are calculated by applying Bragg's equation. The measuring error $\Delta(d_{hkl})$ to $d_{hkl}$ is calculated using Bragg's equation based on the absolute error $\Delta(2\theta)$ that is assigned to the measurement of 2$\theta$. An absolute error of $\Delta(2\theta)$ that is equal to ±0.02° is commonly allowed. The relative intensity $I/I_o$ assigned to each value of $d_{hkl}$ is measured according to the height of the corresponding diffraction peak. The X-ray diffraction diagram of the MIL-53-Al—$N_3$ crystallized hybrid solid according to the invention comprises at least the lines with given values of $d_{hkl}$ in Table 1. In the column of $d_{hkl}$, the mean values for the inter-recticular distances are indicated in angstroms (Å). Each of these values is to be assigned the measuring error $\Delta(d_{hkl})$ of between ±0.3 Å and ±0.01 Å.

BRIEF DESCRIPTION OF THE DRAWING

FIG. 1 is an x-ray diffraction diagram of a solid according to the invention.

TABLE 1

Mean Values for $d_{hkl}$ and Relative Intensities Measured on an X-Ray Diffraction Diagram of the MIL-53-Al—$N_3$ Crystallized Hybrid Solid.

| 2 Theta (°) | $d_{hkl}$ (Å) | $I/I_o$ |
|---|---|---|
| 9.36 | 9.44 | mf |
| 11.94 | 7.40 | FF |
| 17.34 | 5.11 | F |
| 17.83 | 4.97 | mf |
| 19.92 | 4.45 | f |
| 22.06 | 4.03 | f |
| 23.98 | 3.71 | mf |
| 25.31 | 3.52 | f |
| 26.36 | 3.38 | mf |
| 29.63 | 3.01 | f |
| 32.86 | 2.72 | f |
| 33.55 | 2.67 | ff |
| 34.84 | 2.57 | ff |
| 36.04 | 2.49 | ff |
| 40.54 | 2.22 | ff |
| 40.89 | 2.21 | ff |
| 44.29 | 2.04 | ff |
| 51.02 | 1.79 | ff | where FF=Very High; F=High; m=Medium; mf=Medium Low; f=Low; and ff=Very Low. The relative intensity $I/I_o$ is provided in relation to a relative intensity scale where a value of 100 is assigned to the most intense line of the X-ray diffraction diagram: ff<15; 15≤f<30; 30≤mf<50; 50≤m<65; 65≤F<85; and FF≥85.

The MIL-53-Al—$N_3$ crystallized hybrid solid according to the invention has a crystalline structure with a base or topology that is characterized by its X-diffraction diagram provided by FIG. 1. The crystalline structure of the MIL-53-Al—$N_3$ crystallized hybrid solid according to the invention is identical to the one that is exhibited by the MIL-53-Al—$NH_2$ crystallized hybrid solid that is described in the literature (T. Ahnfeldt; D. Gunzelmann; T. Loiseau; D. Hirsemann; J. Senker; G. Ferey, N. Stock, *Inorganic Chemistry*, 2009, 48, 7, 3057-3064) and from which said MIL-53-Al—$N_3$ solid is obtained, in accordance with the process for preparation described farther down in this description.

The MIL-53-Al—$NH_3$ crystallized hybrid solid according to the invention has a three-dimensional structure in which the inorganic network—formed by $Al^{3+}$-cation-based metal centers that perform the role of connectors—is linked together by deprotonated terephthalic ligands (—$O_2C$—$C_6H_3$—$N_3$—$CO_2$—) that carry an $N_3$ azide group on the aromatic cycle. An essential characteristic of the MIL-53-Al—$N_3$ crystallized hybrid solid according to the invention resides in the presence of the azide group on the aromatic cycle of each of the deprotonated terephthalic ligands, more specifically called 2-azido-terephthalate ligands (denoted $N_3$-bdc). The structure that is obtained, identical to the one of the MIL-53-Al—$NH_2$ solid, is a three-dimensional structure in which the one-dimensional inorganic chains with an —Al—O(H)— pattern are linked to one another by deprotonated terephthalic ligands ($O_2C$—$C_6H_3$—$N_3$—$CO_2$). Each aluminum atom is hexa-coordinated and is surrounded by two oxygen atoms of the hydroxyl groups that are located in apical position and by four oxygen atoms that are obtained from four $N_3$-bdc deprotonated terephthalic ligands that are located in equatorial position. In addition, each organic ligand is connected to four aluminum atoms (two pairs of close aluminum atoms).

The MIL-53-Al—$N_3$ crystallized hybrid solid according to the invention thus has a chemical composition that has Al(OH)(—$O_2C$—$C_6H_3$—$N_3$—$CO_2$—) for its base pattern. This pattern is repeated n times, with the value of n based on the crystallinity of said solid.

The MIL-53-Al—$N_3$ crystallized hybrid solid according to the invention has also been characterized by Fourier Transform Infrared (FT-IR) spectroscopy and by $^1$H NMR in such a way as to verify the presence of the azide group on each of the deprotonated terephthalate ligands. Thus, the spectrum that is obtained by FT-IR has a characteristic band of the azide group at 2,122 $cm^{-1}$. The $^1$H-NMR analysis is implemented on a sample of said MIL-53-Al—$N_3$ hybrid solid according to the invention, after digestion and total dissolution of said sample in a $DCl/D_2O/DMSO$-$d_6$ deuterated mixture according to an operating mode described in the literature (Z. Q. Wang, S. M. Cohen, *Journal of the American Chemical Society*, 2007, 129, 12368-12369). Coupled to the FT-IR analysis, the $^1$H-NMR analysis confirms the presence of the $N_3$ azide group on the aromatic cycle of the deprotonated terephthalic ligand: δ=7.73-7.83 ppm, m, 3H, ArH. The 3 protons leading to the detection of the multiplet correspond to the 3 protons carried by the aromatic cycle of the 2-azido-terephthalate ($N_3$-bdc) ligand.

This invention also has as its object a process for the preparation of the MIL-53-Al—$N_3$ crystallized hybrid solid. Said MIL-53-Al—$N_3$ solid is prepared from the MIL-53-Al—$NH_2$ crystallized hybrid solid that is described in the literature (T. Ahnfeldt; D. Gunzelmann; T. Loiseau; D. Hirsemann; J. Senker; G. Ferey; N. Stock, *Inorganic Chemistry*, 2009, 48, 7, 3057-3064). Said MIL-53-Al—$NH_2$ solid has a three-dimensional structure in which the one-dimensional inorganic chains with an —Al—O(H)— pattern are linked to one another by the 2-aminoterephthalate ligands that carry an —$NH_2$ amine group on the aromatic cycle ($O_2C$—$C_6H_3$—$NH_2$—$CO_2$, $NH_2$-BDC ligand). Each aluminum atom is hexa-coordinated and is surrounded by two oxygen atoms of the hydroxyl groups that are located in apical position and four oxygen atoms that are obtained from four 2-aminoterephthalate ligands that are located in equatorial position. In addition, an organic ligand is connected to four aluminum atoms (two pairs of close aluminum atoms). The MIL-53-Al—$NH_2$ crystallized hybrid solid has a chemical composition that has Al(OH)(—$O_2C$—$C_6H_3$—$N_2$—$CO_2$—) for a base pattern. This pattern is repeated n times, with the value of n based on the crystallinity of said solid.

A method for preparation of said MIL-53-Al—$N_3$ solid is described in the literature (T. Ahnfeldt; D. Gunzelmann; T. Loiseau; D. Hirsemann; J. Senker; G. Ferey; N. Stock, *Inorganic Chemistry*, 2009, 48, 7, 3057-3064). The process for preparation of the invention makes possible the replacement of the —$NH_2$ amine group that is present in the MIL-53-Al—$NH_2$ solid by the $N_3$ azide group. The process for preparation according to the invention comprises at least the following stages:

i/ Introduction, into a polar solvent S, of at least said MIL-53-Al—$NH_2$ crystallized hybrid solid, at least one organic compound Q that contains an $N_3$ azide group, and at least one intermediate reagent R that contains an $NO_2$ nitrite group in a proportion such that the reaction mixture has the following molar composition, based on a molar equivalent of the —$NH_2$ group that is present in the MIL-53-Al—$NH_2$ solid:

1MIL-53-Al—$NH_2$:45-135R:40-120Q:100-400S ii/ Reaction of said reaction mixture at a temperature of between 0 and 100° C. for a period of between 1 and 24 hours to obtain said MIL-53-Al—$N_3$ crystallized hybrid solid, iii/ Filtration, and then washing of said MIL-53-Al—$N_3$ crystallized hybrid solid, iv/ Drying of said MIL-53-Al—$N_3$ crystallized hybrid solid.

In accordance with said stage i) of said process for the preparation of the MIL-53-Al—$N_3$ crystallized hybrid solid according to the invention, said MIL-53-Al—$NH_2$ crystallized hybrid solid is dried in advance before being introduced into said polar solvent. The drying of said MIL-53-Al—$NH_2$ crystallized hybrid solid is advantageously implemented at a temperature of between 20 and 100° C. for a period of between 1 and 24 hours, very advantageously for a period of approximately 12 hours. The drying is done in air or under vacuum, in a preferred manner under vacuum.

In accordance with said stage i) of the process for preparation according to the invention, said organic compound Q that contains an $N_3$ azide group is advantageously selected from among trimethylsilyl azide (TMS-$N_3$, $(CH_3)_3SiN_3$), triflyl azide (Tf$N_3$, where Tf=$CF_3SO_2$), p-tosyl azide (Ts$N_3$ or 4-methylbenzenesulfonyl azide of formula $C_6H_4(CH_3)SO_2N_3$), and sodium azide (Na$N_3$). In a preferred manner, said organic compound Q that contains an $N_3$ group is trimethylsilyl azide (TMS-$N_3$).

In accordance with said stage i) of the process for preparation according to the invention, said intermediate reagent R that contains an $NO_2$ nitrite group is advantageously selected from among alkaline reagents such as sodium nitrite (Na$NO_2$) and calcium nitrite (Ca($NO_2$)$_2$), metal reagents, and alkoyl-type reagents such as tert-butyl-nitrite (tBuONO, $(CH_3)_3CONO$). In a very preferred manner, said intermediate reagent R that contains an $NO_2$ nitrite group is tert-butyl-nitrite (tBuONO). Said intermediate reagent R that contains an $NO_2$ nitrite group ensures the formation of a diazonium salt that next reacts with the organic compound Q.

The polar solvent S that is used in said stage i) of the process for preparation according to the invention is preferably volatile. It is very advantageously selected from among tetrahydrofuran (THF), acetonitrile, and ethanol.

In accordance with said stage i) of the process for preparation according to the invention, the reaction mixture preferably has the following molar composition, based on a molar equivalent of the —$NH_2$ group that is present in the MIL-53-Al—$NH_2$ solid:

1MIL-53-Al—$NH_2$:70-110R:60-100Q:100-200S

Said reaction stage in accordance with said stage ii) of the process for preparation according to the invention is preferably implemented at a temperature of between 0 and 60° C., and even more preferably at ambient temperature. The reaction mixture is stirred using a magnetic stirring mechanism. The reaction period is between 1 and 24 hours, preferably between 5 and 15 hours, and most often approximately 12 hours. The solid that is obtained at the end of said stage ii) is an MIL-53-Al—$N_3$ crystallized hybrid solid that has an X-ray diffraction diagram that includes at least the lines that are recorded in Table 1.

In accordance with said stage iii) of the process for preparation according to the invention, said MIL-53-Al—$N_3$ crystallized hybrid solid that is obtained at the end of said stage ii) is filtered and then washed with suitable solvents. The washing of said MIL-53-Al—$N_3$ solid is preferably implemented by a first washing sequence by means of polar solvents, for example ethanol, followed by a second washing sequence by means of volatile solvents, for example dichloromethane. The washing stage of said MIL-53-Al—$N_3$ crystallized hybrid solid is initiated, for example, by implementing 3 sequences of washing with ethanol followed by 3 sequences of washing with $CH_2Cl_2$ dichloromethane.

In accordance with said stage iv) of the process for preparation according to the invention, said MIL-53-Al—$N_3$ crystallized hybrid solid is dried. The drying is done in air or under vacuum at between 20° C. and 100° C. In a preferred manner, the drying is done at ambient temperature under vacuum for a period that varies between 1 and 24 hours, most often approximately 12 hours.

The solid that is obtained at the end of stage iv) is identified as being the MIL-53-Al—$N_3$ crystallized hybrid solid according to the invention. The analyses that are implemented on the solid that is obtained at the end of the process for preparation according to the invention demonstrate the effectiveness of the treatment by post-modification. In particular, the analysis that is implemented on the MIL-53-Al—$N_3$ crystallized hybrid solid by XRD demonstrates that the treatment of functionalization by post-modification that makes it possible to replace the —$NH_2$ amino group by the —$N_3$ azide group does not affect the structure and the crystallinity of the solid. The FT-IR analysis reveals the presence of the —$N_3$ azide group on each of the terephthalate ligands in the MIL-53-Al—$N_3$ solid. Coupled to the FT-IR analysis, the $^1$H-NMR analysis confirms the presence of the —$N_3$ azide group on each of the terephthalate ligands in the MIL-53-Al—$N_3$ solid and makes it possible to estimate the rate of modification of the amino groups into $N_3$ azide groups. In accordance with the process for preparation according to the invention, this rate of modification is very high, i.e., at least equal to 95%, and preferably at least equal to 98%. The rate of modification is calculated by quantifying the decrease in the relative area of the signals of aromatic protons of the MIL-53-Al—$NH_2$ form relative to those of the MIL-53-Al—$N_3$ form. The $^1$H-NMR spectrum of the MIL-53-Al—$N_3$ solid according to the invention has new signals that are linked to the appearance of an integral multiplet for 3 protons, which correspond to the 3 protons that are carried by the aromatic cycle of the 2-azido-terephthalate ($N_3$-bdc) ligand.

EXAMPLES

The MIL-53-Al—$NH_2$ and MIL-53-Al—$N_3$ crystallized hybrid solids that are obtained at the end of the implementation of the preparation protocols illustrated by the following Examples 1 and 2 have been analyzed by X-ray diffraction, by Fourier Transform Infrared (FT-IR) spectroscopy, and by nuclear magnetic resonance of hydrogen ($^1$H NMR).

The X-ray diffraction diagrams are obtained by radiocrystallographic analysis by using the conventional powder method by means of a Bruker D5005 diffractometer (Cu K$\alpha_{1+2}$=0.15418 nm) that is equipped with a graphite curved rear monochromator and a scintillation detector. The analyses of the solids have been recorded with the Debye-Scherrer method from 3 to 80° (2θ) with a pitch of 0.02° for 8 seconds.

The infrared analyses are done using KBr pellets on a Bruker Vector 22 FT-IR device with a useful operating range of: 4,000-400 $cm^{-1}$.

The nuclear magnetic resonance spectra in solution are obtained using a Bruker Avance 250 NMR spectrometer (5.87 T, 250 MHz for $^1$H).

Example 1

Preparation of the MIL-53-Al—$NH_2$ Crystallized Hybrid Solid 120 mg (0.66 mmol) of 2-amino-1,4-benzene dicarboxylic acid (Alfa Aesar, 99%) in suspension in 28 ml (1.55 mmol) of distilled water is placed in a PTFE receptacle with an inside volume of 40 ml, and 1.10 ml (0.44 mmol) of a hydrated aluminum chloride solution ($AlCl_3.6H_2O$, Aldrich, 98%) at a concentration of 0.4 mol/L and 0.56 ml (0.22 mmol) of an NaOH solution at a concentration of 0.4 mol/L are added thereto. The mixture is stirred for 5 minutes using a magnetic stifling mechanism. The PTFE receptacle is then transferred into an autoclave and then heated without being stirred at 110° C. for 24 hours. After cooling, the crystallized solid that is obtained is washed with water and then with a hot DMF solution (Aldrich, 99.8%), and with dichloromethane (ACROS ORGANICS, 99.99%). After drying in the oven (air) at 80° C. for one night, a powder that consists of MIL-53-Al—$NH_2$ crystals is obtained.

Said MIL-53-Al—$NH_2$ crystallized hybrid solid is analyzed by X-ray diffraction, by Fourier Transform Infrared spectroscopy, and by nuclear magnetic resonance of hydrogen ($^1$H NMR).

The X-ray diffraction analysis reveals that said solid that is obtained in Example 1 is identified as consisting of MIL-53-Al—$NH_2$ solid: the diffractogram that is carried out on said solid is identical to the one that corresponds to the MIL-53-Al—$NH_2$ (it) that is presented in *Inorganic Chemistry*, 2009, 48, 7, 3057-3064.

The FT-IR analysis reveals the presence of the —$NH_2$ amino group in the MIL-53-Al—$NH_2$ IR (KBr pellet) solid, ν($cm^{-1}$): 3498, 3386, 2951, 1685, 1581, 1487, 1436, 1402, 1333, 1256, 1000, 777, 640, 597, 546, 452. The bands at 3,498 and 3,386 $cm^{-1}$ are attributed to the amine group.

The $^1$H-NMR analysis is implemented on a sample of the MIL-53-Al—$NH_2$ solid, after digestion and total dissolution of the sample in a $DCl/D_2O/DMSO$-$d_6$ deuterated mixture according to the operating mode that is described in the literature (Z. Q. Wang, S. M. Cohen, *Journal of the American Society*, 2007, 129, 12368-12369): 10 mg of MIL-53-Al—$NH_2$ hybrid solid is digested and dissolved in 1.5 ml of deuterated DMSO and 0.2 ml of a dilute DCl solution (prepared from a solution that contains 0.23 ml of $DCl/D_2O$ at 35% and 1 ml of deuterated DMSO).

Coupled to the FT-IR analysis, the $^1$H-NMR analysis also reveals the presence of the —$NH_2$ amino group in the MIL-53-Al—$NH_2$ solid. $^1$H NMR, 250 MHz, t.a, δ (ppm/($DCl/D_2O/DMSO$-$d_6$)): 6.90 (d, 1H, J=8 Hz); 7.03 (s, 1H); 7.56 (d, 1H, J=8 Hz).

Example 2

Preparation of the MIL-53-Al—$N_3$ Solid by Post-Modification of the MIL-53-Al—$NH_2$ Hybrid Solid 80 mg (0.36 mmol equivalent of —$NH_2$) of MIL-53-Al—$NH_2$ solid, obtained at the end of the process that is illustrated in Example 1, is vacuum-dried for 12 hours at 85° C. and then placed in a pill machine (8 ml capacity) with 3 ml (51.3 mmol, 142.5 eq) of ethanol (Fluka, 99.8%), 3.8 ml (32 mmol, 89 eq) of tBuONO (Aldrich, 90%), and 3.6 ml (28 mmol, 78 eq) of TMS-$N_3$ (Aldrich, 95%). After 12 hours of reaction at ambient temperature, the solid is filtered and then washed three times with 8 ml of ethanol (Fluka, 99.8%), and then three times with 8 ml of $CH_2Cl_2$ (ACROS ORGANICS, 99.99%) before being vacuum-dried at ambient temperature for 12 hours.

The solid that is obtained has been analyzed by X-ray diffraction and identified as consisting of MIL-53-Al—$N_3$ crystallized hybrid solid: the diffractogram that is implemented on the MIL-53-Al—$N_3$ solid is the one that is provided by FIG. 1. The analysis that is implemented on the MIL-53-Al—$N_3$ crystallized hybrid solid by XRD demonstrates that the post-modification treatment that makes it possible to replace the —$NH_2$ amino group by the —$N_3$ azide group does not affect the structure and the crystallinity of the solid.

The FT-IR analysis reveals the presence of the —$N_3$ azide group on each of the terephthalate ligands in the MIL-53-Al—$N_3$ solid. The spectrum that is obtained by FT-IR has a characteristic band of the azide group at 2,122 $cm^{-1}$. The bands at 3,498 and 3,386 $cm^{-1}$ that correspond to the —$NH_2$ group have disappeared.

The $^1$H-NMR analysis is implemented on a sample of the MIL-53-Al—$N_3$ hybrid solid, after digestion and total dissolution of the sample in a $DCl/D_2O/DMSO-d_6$ deuterated mixture according to an operating mode that is described in the literature (Z. Q. Wang, S. M. Cohen, *Journal of the American Chemical Society,* 2007, 129, 12368-12369): 10 mg of MIL-53-Al—$N_3$ hybrid solid is digested and dissolved in 1.5 ml of deuterated DMSO and 0.2 ml of a dilute DCl solution (prepared from a solution that contains 0.23 ml of $DCl/D_2O$ at 35% and 1 ml of deuterated DMSO).

The $^1$H-NMR analysis confirms the presence of the $N_3$ azide group in the aromatic cycle of the deprotonated terephthalic ligand. $^1$H NMR, 250 MHz, t.a, δ (ppm/($DCl/D_2O$/DMSO-$d_6$)): δ=7.73-7.83 ppm, m, 3H, ArH. The 3 protons that lead to the detection of the multiplet correspond to 3 protons that are carried by the aromatic cycle of the 2-azidoterephthalate ($N_3$-bdc) ligand.

The comparison of the IR and $^1$H-NMR spectra that are obtained for the MIL-53-Al—$NH_2$ solid and for the MIL-53-Al—$N_3$ solid demonstrates the effectiveness of said post-modification treatment—with the comparison of $^1$H-NMR spectra obtained for the MIL-53-Al—$NH_2$ solid and for the MIL-53-Al—$N_3$ solid making it possible to estimate at 98% the rate of modification of the amino groups into $N_3$ azide groups—by quantifying the decrease of the relative area of the signals of the MIL-53-Al—$NH_2$ solid relative to those of the MIL-53-Al—$N_3$ solid.

The invention claimed is:

1. A MIL-53-Al—$N_3$ crystallized hybrid solid with an organic-inorganic matrix, of a three-dimensional structure, containing an inorganic network of aluminum-based metal centers that are connected to one another by organic ligands that consist of the entity
—$O_2C$—$C_6H_3$—$N_3$—$CO_2$— ($N_3$-bdc ligand), whereby said solid exhibits an X-ray diffraction diagram that includes at least the lines that are recorded in the table below:

| 2 Theta (°) | $d_{hkl}$ (Å) | $I/I_o$ |
|---|---|---|
| 9.36 | 9.44 | mf |
| 11.94 | 7.40 | FF |
| 17.34 | 5.11 | F |
| 17.83 | 4.97 | mf |
| 19.92 | 4.45 | f |
| 22.06 | 4.03 | f |
| 23.98 | 3.71 | mf |
| 25.31 | 3.52 | f |
| 26.36 | 3.38 | mf |
| 29.63 | 3.01 | f |
| 32.86 | 2.72 | f |
| 33.55 | 2.67 | ff |
| 34.84 | 2.57 | ff |
| 36.04 | 2.49 | ff |
| 40.54 | 2.22 | ff |
| 40.89 | 2.21 | ff |
| 44.29 | 2.04 | ff |
| 51.02 | 1.79 | ff | where FF=Very High; F=High; m=Medium; mf=Medium Low; f=Low; and ff=Very Low, with the relative intensity $I/I_o$ being provided in relation to a relative intensity scale where a value of 100 is assigned to the most intense line of the X-ray diffraction diagram: ff<15; 15≤f<30; 30≤mf<50; 50≤m<65; 65≤F<85; and FF≥5, and whereby H—N MR analysis confirms the presence of an $N_3$ azid group on an aromatic cycle of a deprotonated terephthalic ligand: δ=7.73-7.83 ppm, m, 3H, ArH, 3 protons leading to the detection of the multiplet corresponding to 3 protons carried by the aromatic cycle of the ($N_3$-bdc) ligand.

2. The MIL-53-Al—$N_3$ crystallized hybrid solid according to claim 1, such that it exhibits a crystalline structure that is identical to the one of the MIL-53-Al—$NH_2$ crystallized hybrid solid.

3. The MIL-53-Al—$N_3$ crystallized hybrid solid according to claim 1, such that each organic ligand is connected to four aluminum atoms.

4. The MIL-53-Al—$N_3$ crystallized hybrid solid according to claim 1, such that each aluminum atom is surrounded by two oxygen atoms of hydroxyl groups that are located in apical position and four oxygen atoms that are obtained from four $N_3$-bdc deprotonated terephthalic ligands that are located in equatorial position.

5. The MIL-53-Al—$N_3$ crystallized hybrid solid according to claim 1, such that it exhibits a chemical composition that has Al(OH)(—$O_2C$—$C_6H_3$—$N_3$—$CO_2$—) for a base pattern.

6. A process for the preparation of an MIL-53-Al—$N_3$ crystallized hybrid solid according to claim 1, starting from an MIL-53-Al—$NH_2$ crystallized hybrid solid, said process comprising at least the following stages:

i/ Introduction, into a polar solvent S, of at least said MIL-53-Al—$NH_2$ crystallized hybrid solid, at least one organic compound Q that contains an $N_3$ azide group, and at least one intermediate reagent R that contains an $NO_2$ nitrite group in a proportion such that the reaction mixture has the following molar composition, based on a molar equivalent of the —$NH_2$ group that is present in the MIL-53-Al—$NH_2$ solid:

1MIL-53-Al—$NH_2$:45-135R:40-120Q:100-400S ii/ Reaction of said reaction mixture at a temperature of between 0 and 100° C. for a period of between 1 and 24 hours to obtain said MIL-53-Al—$N_3$ crystallized hybrid solid, iii/ Filtration, and then washing of said MIL-53-Al—$N_3$ crystallized hybrid solid, iv/ Drying of said MIL-53-Al—$N_3$ crystallized hybrid solid.

7. The process for preparation according to claim 6, such that said MIL-53-Al—$NH_2$ crystallized hybrid solid is dried in advance before being introduced into said polar solvent.

8. The process for preparation according to claim 6, such that said organic compound Q that contains an $N_3$ azide group is selected from among trimethylsilyl azide (TMS-$N_3$), triflyl azide (Tf$N_3$), p-tosyl azide (Ts$N_3$), and sodium azide (Na$N_3$).

9. The process for preparation according to claim 6, such that said intermediate reagent R that contains an $NO_2$ nitrite group is tert-butyl-nitrite (tBuONO).

10. The process for preparation according to claim 6, such that said polar solvent S is selected from among tetrahydrofuran (THF), acetonitrile and ethanol.

11. The process for preparation according to claim 6, such that said reaction mixture has the following molar composition, based on a molar equivalent of the —$NH_2$ group that is present in the MIL-53-Al—$NH_2$ solid:

1MIL-53-Al—$NH_2$:70-110R:60-100Q:100-200S.

12. The process for preparation according to claim 6, such that said stage ii) is implemented at ambient temperature.

13. The process for preparation according to claim 6, such that the period of said stage ii) is between 5 and 15 hours.

* * * * *